United States Patent [19]

Mottram

[11] Patent Number: 5,952,267
[45] Date of Patent: Sep. 14, 1999

[54] BETAINE OSMOLYTE REGULATOR FOR COTTON

[75] Inventor: Malcolm Mottram, Romsey, Australia

[73] Assignee: AB Tall (Holdings) Pty. Ltd., Australia

[21] Appl. No.: 08/817,117

[22] PCT Filed: Sep. 7, 1995

[86] PCT No.: PCT/AU95/00590

§ 371 Date: Aug. 1, 1997

§ 102(e) Date: Aug. 1, 1997

[87] PCT Pub. No.: WO96/14749

PCT Pub. Date: May 23, 1996

[30] Foreign Application Priority Data

Nov. 15, 1994 [AU] Australia ................. PM 9425
Aug. 7, 1995 [AU] Australia ................. PM 4615

[51] Int. Cl.$^6$ ............... A01N 33/12; A01N 37/44
[52] U.S. Cl. .................... 504/320; 504/345
[58] Field of Search ..................... 504/320, 345

[56] References Cited

FOREIGN PATENT DOCUMENTS

| 0 373 314 | 6/1990 | European Pat. Off. |
| 259 123 | 8/1988 | Germany |
| 277 832 | 4/1990 | Germany |
| 277 833 | 4/1990 | Germany |
| 301 775 | 12/1993 | Germany |
| WO 93/17556 | 9/1993 | WIPO |

OTHER PUBLICATIONS

Hanson et al., Chemical Abstract No. 52227g, "Replacement of Glycine Betaine by β–Alanine Betaine, Choline–O–Sulphate...", vol. 123, No. 5, Jul. 31, 1995, p. 549.

Naidu et al., "Amino Acid and Glycine Betaine Accumulation in Cold–Stressed Wheat Seedlings", Phytochemistry, vol. 30, No. 2, pp. 407–409 1991.

Krishnamurthy et al., "Accumulation of Choline and Glycinebetaine in Salt–Stressed Wheat Seedlings", Current Science, vol. 59, No. 2, Jan. 25, 1990, 111–112.

Derwent Abstract Accession No. 89–104862/14, Class C02, JP 01052703 A, Nippon Zoki Pharm KK, Feb. 28, 1989.

Rhodes, D., and A. D. Hanson. "Quaternary ammonium Tertiary sulfonium compounds in higher plants". Annu. Rev. Plant Physiol. Plant Mol. Biol. 44:357–384, 1993.

Golan–Goldhirsh, A. B. Hankamer and S. H. Lips. "Hydroxyproline and proline content of cell walls of sunflower, peanut and cotton grown under salt stress". Plant Science 69:27–32, 1990.

*Primary Examiner*—S. Mark Clardy
*Attorney, Agent, or Firm*—Nixon & Vanderhye

[57] ABSTRACT

Application of an osmolyte regulator alleviates or combats the effects of stress developing in plants, particularly cotton plants. The osmolyte regulator is preferably glycine betaine and is applied to the growing plants in a dosage of from 0.1 to 10.0 kg/ha. Typically, the osmolyte regulator is applied at the initiation of flowering or shortly thereafter. Application of the osmolyte regulator increases the yield of the plant, thereby increasing the economic value of the plant by reducing the adverse effects of stress.

27 Claims, No Drawings

BETAINE OSMOLYTE REGULATOR FOR COTTON

This application has been filed under 35 USC 371 as the national stage of international application PCT/AU95/00590 filed Sep. 7, 1995.

The present invention relates generally to agriculture and in particular to methods of improving or controlling the growth of crops. More particularly, the present invention relates to methods of controlling stress and related conditions in plants during the growth of the plant, particularly in the early stages of growth and more particularly where the plant is cotton. Even more particularly, the present invention relates to the use of an osmolyte regulator, particularly glycine betaine, to control stress in growing cotton so as to increase the yield of cotton either by increasing the amount of cotton produced per plant or reducing the time taken to obtain mature cotton crops suitable for harvesting. The present invention finds particular application in methods of administering glycine betaine as the osmolyte regulator to control stress in growing cotton plants.

Although the present invention will be described with particular reference to the use of glycine betaine as one example of an osmolyte regulator administered to the leaves of cotton plants to control stress in the plants, it is to be noted that the scope of the present invention is not restricted to the described embodiment but rather the present invention is more extensive so as to include the use of other osmolyte regulators, to other ways of administering the regulators, and to other uses of the chemical compounds than as osmolyte regulators, and to the use of the osmolyte regulators with other plants.

Cotton is a crop having considerable economic value. As cotton plants grow the are often subjected to stress in one or other forms. The plants exhibit being subjected to stress by shedding flower buds (known as "squares"), flowers and bolls. Consequently, the development of stress within the plants is easily monitored by being readily observable and demonstrable. Squares are most readily shed and bolls are least readily shed when plants are experiencing stress. The shedding of squares, flowers and bolls is thus an indication of the amount of stress to which the cotton plants are being subjected. The main causes of stress, and hence shedding, include too much or too little water, inadequate nutrition, low light intensity, or low temperatures, and the like. As an example, cotton plants readily shed squares in cloudy weather whereas the growth and development of cotton is enhanced by heat, provided it is not too excessive.

During the growth stages, cotton crops are frequently subjected to stress, particularly cotton crops which are irrigated, despite the use of sophisticated equipment to monitor moisture and water levels being supplied to and developing within the plants and to measure the amount of nutrients being supplied to the growing crop.

The development of stress in growing cotton plants hinders or otherwise reduces the amount of cotton produced by the plant which reduces the economic worth of the plant. Clearly, the more cotton produced by a plant, the more valuable is the crop. Therefore, any improvement in yield or the amount of cotton produced by the plant is beneficial. The improvement in the amount of cotton produced by the crop can be either an increase in the yield or amount of cotton being produced per plant, or a decrease in the amount of time that a cotton plant requires to mature to produce harvestable cotton. By retaining a higher proportion of squares a crop will reach a given yield earlier than a crop retaining a lower proportion of the squares, and thus can be harvested earlier. The result is an earlier crop that can be "finished" and harvested earlier under drier and more favourable conditions than a later developing crop which is more difficult to harvest.

Earlier harvesting of cotton plants improves the lint quality and gin "out-turn" of the cotton being produced and hence increases the price and profit of the crop.

Furthermore, as crops mature into cotton at different rates depending on circumstances, at any one time there can be a range of cotton bolls. Usually more than a single picking of the cotton is required owing to the different rates of maturity of individual bolls. Therefore, if the age range of the bolls producing the cotton can be reduced, the proportion of cotton harvested in the first pick of cotton will be greater than for late developing crops having a wide range of ages of the bolls. If all of the cotton can be picked in a single pass or harvest, the economic value of the crop will be considerably enhanced. Therefore, there is a need to control the growth rate of cotton to improve its yield by either obtaining a higher yield of cotton per plant or obtaining a predetermined yield or attaining a mature boll more quickly and uniformly over the crop.

Cotton can be grown under irrigation conditions. However, with increases in charges for irrigation water, the profit obtained from growing cotton will be reduced. If irrigation systems are not used but rather cotton is grown on "dry" land, i.e. without extensive use of irrigation, more effective control over the amount of water and moisture provided to the plants will be required in order to prevent or reduce the stress developed or induced in the plants by using too little or too much water.

Cotton is most susceptible to stress during flowering and boll formation and the critical time at which stress in the growing cotton plants should be controlled is about two to six weeks after first flowering.

Therefore, with the increasing use of dry land cotton growing, there is a need to be able to control the amount of stress induced in cotton plants due to having too little or too much water or inadequate nutrition. The use of osmolyte regulators in accordance with the present invention sets out to control stress in growing cotton plants to improve the yield of the plant, particularly stress induced (i) from using too little or too much water, (ii) from being subjected to too low temperatures, and more particularly, (iii) from exposure to stress inducing environments generally in the critical growing period.

Therefore, it is an aim of the present invention to provide a method of administering an osmolyte regulator to a plant, particularly a cotton plant for controlling the stress induced or developed in the growing plant so as to overcome or at least reduce one or more of the drawbacks of growing cotton, and in particular to increase the yield of the plant.

According to one aspect of the present invention there is provided a method of controlling stress in a growing plant comprising administering an effective amount of an osmolyte regulator to the plant such that stress induced or developing in the plant can be controlled to a satisfactory level in order to enhance the growth of the plant to provide a greater yield or to mature plants more quickly or both, thereby increasing the economic value of the plant.

Typically, the plant to which the osmolyte regulator of the present invention is administered is cotton. More typically, the cotton can be of any species of cotton. Typical species of cotton are Siokra L-22, Siokra L-23, CS-50 which is a high yielding broader leaf variety in contrast to ofra leaved varieties, or the like. However, it is to be noted that any plant species, not just cotton, can be treated by the methods of the present invention.

Typically, the osmolyte regulator is an organic solute, a compatible solute, an amino acid, a betaine, a sugar, a polyol, or related compounds to the foregoing, and the like. More typically, the osmolyte regulator is an ammonio compound, such as a N-methyl substituted amino acid, proline, choline or a betaine, such as glycine betaine (oxyneurin) and other betaine member compounds including the sulphonio analogues of the betaines. Other betaines include proline betaine, β-alanine betaine, tryptophan betaine, histidine betaine, 2-mercaptohistidine betaine, and the like. Even more typically, the osmolyte regulator is a nitrogenous compatible solute, such as stachydrine, trigonelline, homostachydrine (pipecolate betaine).

It is to be noted that particularly preferred osmolyte regulators are the betaines, particularly the glycine derivative. Betaine refers to fully N-methylated amino acids. Glycine betaine has three methyl groups attached to the nitrogen atom of the glycine molecule and is usually called betaine, glycino-betaine or trimethyl glycine and has the following structural formula:

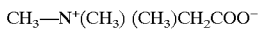

$CH_3-N^+(CH_3)(CH_3)CH_2COO^-$

Other osmolytes or osmoregulators include glycine, methylene glycine, dimethyl glycine, glutamic acid, γ-aminobutyric acid, trimethylamine γ-butyric acid, or the like.

Typically, the osmolyte regulator is administered alone or in combination with one or more other materials. Typically, the other materials include additives such as wetting agents, other adjuvants, defoliants, growth regulators, pesticides, nutrients and the like. The other material can be added separately or in combination with the osmolyte regulator. Even more typically, the osmolyte regulator and other material have a synergistically beneficial effect on the plant.

Typically, in slow drying conditions the regulator is preferably applied with a wetting agent, such as for example PLUS 50 (obtainable from Ciba-Geigy), or is applied in combination with a wetting agent, mineral oil and/or vegetable oil, particularly in fast drying conditions. Although many types of mineral oil or vegetable oils may be used, specific examples of the mineral oil include DC-TRON (a registered trade mark of AMPOL Australia Ltd) which is a narrow range boiling point mineral oil, whereas specific examples of the vegetable oil include rapeseed based vegetable oils such as SYNETROL.

Typically, the amount of osmolyte regulator, typically glycine betaine, administered to the growing cotton plant is such so as to increase the retention of fruiting forms or bolls in cotton thereby increasing the yield of the cotton plants.

Typically, the stress induced or developed in the cotton plant includes environmental stresses such as, for example, stress related to temperature, water, salinity, light, nutritional stresses and the like. More typically, the stress induced results from too little or too much water, too low a temperature, too high salt concentration, too low light intensity, too low nitrogen concentration, and the like.

Typically, the glycine betaine is administered to the cotton plants in a dose of from about 0.1 to 30.0 kg/ha, typically from 0.1 to 10.0 or 20.0 kg/ha, preferably from 0.5 to 7.0 kg/ha with typical dosages being about 0.5, 1.5, 2.5, 3.5 kg/ha and preferable dosages being between about 2.0 to 4.0 kg/ha, more preferably between about 2.5 to 3.5 kg/ha. More typically, the regulator is applied externally or exogenously to the plants, such as for example to the leaves of the plant.

Typically, the osmolyte regulator is applied to the crops early in the life of the crops. More typically, the glycine betaine is applied to the cotton plants at 77 or 98 days after planting. It is to be noted that the osmolyte regulator can be administered to the plants at any time from planting until harvesting, including before, during or after flowering of the plants. Typically, the time of application is from the initiation of flowering, such as for example where there is 1 flower per 4 m length of plants present in the plants, until a time from about 5 to 7 days later where there is significant flowering. More typically, the time of administration is at the initiation of flowering or shortly thereafter, such as for example at a time when about 2% of the plants are flowering.

Typically, the use of glycine betaine improves the number of fruit forms developed by the cotton plants by about 35% at about 113 days after planting.

Typically, the use of glycine betaine promotes a significant increase in height of the plants, from about 85 to 110 mm compared to untreated cotton, particularly when used in about or close to optimum dosages, such as at about 3.5 kg/ha.

More typically, the stress induced in the cotton plants which is controlled by the osmolyte regulator of the present invention, is stress induced from having too little or too much water, or too low a temperature.

Typically, the osmolyte regulator is applied to the plants by spraying, more typically spraying of aqueous solution. More typically, the aqueous solution has a concentration of glycine betaine of about three kilograms per 200 liters of water. More typically, the solution containing the regulator of the present invention in water is applied in amounts from about 50 to 200 L/ha, more typically at about 50 to 100 L/ha.

Typically, the more advanced the fruit form of the plant when the osmolyte regulator is applied, the more the plant responds to the addition of the osmolyte regulator, and more control over stress induced in the plant is obtained.

The osmolyte regulator of the present invention is particularly adapted for controlling the effects of stress caused by low temperature. However, it is to be noted that the osmolyte regulator can be added to control the effects of any stress-inducing characteristic of the environment in which the plant is located.

The present invention will now be described by way of example with reference to the following examples which are meant to be illustrative of the present invention and not limiting.

EXAMPLE 1

The object of this example is to determine the effect of foliar applications of glycine betaine on square and boll retention on cotton subjected to a moderate level of moisture stress, under non-limiting nitrogen and virtually pest-free conditions.

Layout of the Trial

The trial used in this example was sited in the third and seventh rows of a block of cotton comprising rows of 300 meters long and 20 rows wide. The cotton was of the Siokra L-22 variety and had a plant density of 8 to 9 plants per meter of row with rows being 1 meter apart. The rows extended in the direction 30° and 210°. A reduced irrigation regime treatment was effected to the third row and normal irrigation regime treatment was effected to the seventh row with the inter-row spaces between rows 1 and 5 being under the reduced irrigation regime and all other inter-row spaces in the block being under the normal irrigation regime. Thus, rows 1 to 5 were subjected to reduced amounts of water and moisture whereas rows 6 to 20 had normal amounts of water and moisture.

The seven treatments under the reduced irrigation regime, denoted as codes A1, . . . , D in Table 1 entitled "Materials applied and timing" were laid out as a modified randomised complete block experiment. In each block, there were two application timings of each dose of the experimental compound which were placed in adjacent plots. The first timing of application of glycine betaine was at 77 days after planting, codes A1, B1, C1 of Table 1, whereas the second timing of application was at 98 days after planting, codes A2, B2, C2 of Table 1.

The plot size was 7.5 meters of row and there was one replicate of each treatment in each of the four blocks. The criteria for determining which plants were to constitute a block was plant height and compactness of the plants within the block. Thus, each block occupied a continuous 52.5 meter length of row that contained plants of similar height. Between each block there was 10 to 20 meters of row containing plants of varying heights that were unsuitable for use in the present trial. A normal irrigation regime plot was placed opposite each central plot of each block.

TABLE 1

Materials Applied and Timing

| Code | Dose of Betaine Glycine kg/ha *1 | Time of Application Days After Planting | Irrigation Regime |
| --- | --- | --- | --- |
| A1 | 1.0 | 77 | Reduced |
| A2 | 1.0 | 98 | Reduced |
| B1 | 3.0 | 77 | Reduced |
| B2 | 3.0 | 98 | Reduced |
| C1 | 5.0 | 77 | Reduced |
| C2 | 5.0 | 98 | Reduced |
| D | 0 | n/a | Reduced |
| E | 0 | n/a | Normal |

*1 "Plus 50" wetting agent added to all sprays at 2 ml/litre. No other materials were applied with the experimental sprays.

TABLE 2

Application of Experimental treatments:

| Application No.: | 1 | 2 |
| --- | --- | --- |
| Treatments Applied: | A1, B1, C1 | A2, B2, C2 |
| Time: | 1915 to 1940 | 2140 to 2205 |
| Date: | | |
| Days After Planting: | 77 | 98 |
| Nozzle Designation: | TX4 | |
| Nozzle Manufacturer: | Spraying Systems Co. | |
| Pressure at Nozzle (kPa): | 225 | |
| Droplet Size VMD (mm) | 125 | |
| Nozzle Discharge (ml/sec) | 41 | |
| Nozzle Swath (cm): | 25 | |
| Ground speed (m/sec): | 0.79 (9.5 seconds/7.5 metre plot) | |
| Spray Volume. (l/ha): | 205 | |
| Water Quality: | Clean, fresh potable water (ex Ord river) pH 69 | |
| Temperature (° C.): | 23 | 24 |
| DT (° C.): | 6 | 5 |
| Relative Humidity (%): | 58 | 65 |
| Wind Speed (m/sec): | nil | 0.4 to 0.7 |
| Wind Bearing: | n/a | 235 to 250 |
| Application Heading: | 210° C. | |
| Spray Drift: | negligible | low, negligible on adjacent plots |
| Foliage Condition: | Dry | |
| Crop Stage: | 0.4% of plants flowering | 57% of plants flowering |
| Crop Condition: | Healthy. No disease | |

Application

The glycine betaine was applied as an aqueous solution by spraying the leaves of the plant. The spraying equipment used was a compressed gas-powered sprayer fitted with a flat boom carrying four nozzles at 25 cm spacings. The parameters of spraying are as shown in Table 2.

Irrigation Regimes

The two different irrigation regimes, i.e. the reduced irrigation regime and the normal regime, were commenced on the plants of the respective blocks at 80 days after planting. Up to this time, the entire block of cotton plants was irrigated at 2, 17, 29, 43, 59 and 70 days after planting. The crop under the normal irrigation regime was then irrigated at 80, 89, 97, 105 and 112 days respectively after planting, while the crop under the reduced irrigation regime was irrigated at 89 and 105 days only after planting.

Two irrigation regimes were imposed on plants that were not treated with glycine betaine, a normal irrigation regime indicated as treatment B in Table 1, and a reduced irrigation regime indicated as treatment D in Table 1. The frequency of the normal irrigation regime was based on the water requirements of cotton which had been planted at the same location in previous seasons. It was anticipated that the plants under this regime, i.e. treatment E of Table 1, would bear the greatest number of fruit forms. However, these plants actually carried the least as will be explained in more detail below with reference to Table 3. This indicates that the plants treated under treatment E were subjected to greater stress than the plants under the reduced irrigation regime. The increased stress was brought about by the increased water added to the plants due to the high rainfall in combination with the normal irrigation. The more frequent irrigations of the normal irrigation regime made the plants more susceptible to cold stress due to low night temperatures as described below and in addition, it waterlogged them for short periods.

Cotton ceases growing when soil and ambient temperatures fall below 12° C. and temperatures below 11° C. damage the plant. Over the 38 days that the trial was conducted, ambient temperatures fell to 12° C. or lower on six nights. The lowest minimum temperatures recorded were 8.5° C. and 8.7° C. at 81 and 82 days after planting respectively. This was immediately after the plants had been irrigated in accordance with the normal irrigation regime, whereas plants under the reduced regime were dry. The combined effect of the excess water and low temperature induced stress in the plants under the normal irrigation regime.

It was calculated that, relative to the plants subjected to reduced irrigation regimes, the growth of the normally irrigated plants was retarded by four to five days, due to the excess moisture causing lower temperatures of the plants. This calculation made no allowance for waterlogging of the plants which would have occurred due to relatively low evaporation during the cool days that followed.

The crop under the normal irrigation regime was definitely waterlogged for two to three days after the irrigation at 89 days after planting. This irrigation was planned to incorporate an application of nitrogenous fertiliser in all plots to ensure that the amount of nitrogenous fertiliser present was not limiting to the growth of the plants. Delaying the application of nitrogenous fertiliser risked that part of the experiment involving the plants under reduced irrigation. Unfortunately, the soil in the normal irrigation plots was still moist. Hence, following irrigation for the plants subjected to the normal irrigation regime, the plants were saturated for at least two days after the soil of the reduced irrigation plots had reached field capacity. This waterlogging, plus the earlier cold stress, combined to retard the growth of the normally irrigated plants by at least a week compared to the reduced irrigated plants. Therefore, it is less valid to compare the results of the plants subjected to treatment E with those subjected to the glycine betaine treatments in the trial. Plants treated with glycine betaine could only strictly be validly compared with plants subjected to treatment D.

Optimum Dose and Time of Application

With particular reference to Table 3 entitled "Effect of the treatments on the numbers of fruit forms, 113 days after planting", the results of each of the treatments A1 to E will now be discussed.

Furthermore, the results of Table 3 indicate that higher doses are required to obtain a given response from younger plants than from older plants. Thus, a preferred feature of the present invention is that the application of the osmolyte

TABLE 3

Effect of the treatments on the numbers of fruit forms, 113 days after planting.

| Code # | Dose of Betaine Glycine kg/ha | Irrigation Schedule | Mean Number per Plant at 113 to 114 days after planting | | | | | | | |
|---|---|---|---|---|---|---|---|---|---|---|
| | | | Bolls | | New Bolls | | White Flowers | | Squares | |
| A1 | 1 | Reduced | 3.6 bc | AB | 6.0 d | C | 1.3 abc | AB | 27.4 b | A |
| A2 | 1 | Reduced | 4.2 cd | BC | 4.7 bc | AB | 0.9 ab | A | 25.2 ab | A |
| B1 | 3 | Reduced | 5.3 d | C | 6.5 d | C | 1.9 c | B | 31.9 c | B |
| B2 | 3 | Reduced | 4.2 cd | BC | 5.8 cd | BC | 1.5 bc | AB | 31.9 c | B |
| C1 | 5 | Reduced | 3.5 bc | AB | 4.0 b | A | 1.1 ab | A | 27.6 ab | AB |
| C2 | 5 | Reduced | 2.9 ab | A | 4.5 b | A | 1.0 ab | A | 25.7 ab | A |
| D | 0 | Reduced | 4.1 cd | BC | 4.3 b | A | 1.1 ab | A | 23.9 ab | A |
| E | 0 | Normal | 2.0 a | — | 2.5 a | — | 0.8 a | — | 22.6 a | — |
| Significance level of F (2-way ANOVA) | | | <0.001 | 0.004 | <0.001 | <0.001 | 0.015 | 0.025 | <0.001 | <0.001 |

| | | | Mean Number per Plant at 113 to 114 days after planting | | | | | | | |
|---|---|---|---|---|---|---|---|---|---|---|
| | | | Bolls + New Bolls | | Bolls + New Bolls + White Flowers | | Bolls + New Bolls + White Flowers + Squares | | % Bolls + New Bolls | |
| A1 | 1 | Reduced | 9.9 | B | 11.5 | B | 39.6 | BC | 25 | A |
| A2 | 1 | Reduced | 9.2 | AB | 10.5 | AB | 36.3 | AB | 25 | A |
| B1 | 3 | Reduced | 12.2 | C | 14.6 | C | 47.1 | C | 26 | A |
| B2 | 3 | Reduced | 10.3 | BC | 12.2 | B | 44.5 | B | 23 | A |
| C1 | 5 | Reduced | 7.7 | A | 9.1 | A | 37.1 | A | 21 | A |
| C2 | 5 | Reduced | 7.7 | A | 9.0 | A | 35.5 | A | 22 | A |
| D | 0 | Reduced | 8.6 | AB | 10.1 | AB | 34.5 | AB | 25 | A |
| E | 0 | Normal | — | — | — | — | — | — | — | — |
| Significance level of F (2-way ANOVA) | | | — | <0.001 | — | <0.001 | — | <0.001 | — | 0.174 |

*1 Letters indicate statistical separation (p = 0.05) Fisher's protected LSD test. Lower case letters apply to all treatments. upper case letters to treatments A to D
All means de-transformed from square roots #A1, B1, C1 applied on day 77. A2, B2, and C2 applied on day 98.
Spray volume 200 l/ha All sprays contained Plus 50 wetting agent at 2 ml/litre.

As can be readily seen from Table 2, there are significantly more fruit forms denoted as bolls, new bolls, white flowers, squares, and combinations thereof, on cotton plants which had been treated with glycine betaine at 3 kg per hectare, which is treatments B1 and B2, than on any other plants. This is evident from a comparison of all treatments provided in Table 3. When the data about the development of fruit forms was compared after the data was pooled across the time of application, it was clear that the treatments involving the addition of glycine betaine improved the amount and time of the development of fruit forms. Specifically, glycine betaine at 1 kg per hectare appeared to increase the number of fruit forms relative to the untreated control, treatment D. Thus, from the information in Table 3, it is clear that 3 kg per hectare was the optimum amount of glycine betaine added to the plants. Doses of glycine betaine above 3 kg per hectare, such as for example 5 kg per hectare of treatments C1 and C2, tended to indicate that excess glycine betaine may have an adverse effect on the growth of cotton.

Regarding the timing of addition of the glycine betaine, the results of Table 3 indicate that the more advanced the fruit form of the cotton plants at the time of application of the glycine betaine, the more the plant responds to the addition of the glycine betaine. However, in order to promote the production and development of fruit forms in the growing cotton plants, the crops can be sprayed earlier rather than later to increase the number of fruit forms.

regulator to the plants occur early in the growing stage of the plants, such as for example before flowering, in order to increase the development of fruit forms of the plant.

From observation of the plants from which the results of Table 3 had been obtained it was clear that almost all of the plants were under stress at almost all time during the growing period, and that the plants which were treated with glycine betaine, such as in treatments A1 to C2, performed significantly better than those of treatments D and E. Thus, it is clear that the addition of glycine betaine is beneficial in controlling stress induced by too much water or moisture and too low a temperature. Furthermore, in treatment E the stress induced in the cotton plants was typically caused by low temperatures. Furthermore, the plants subjected to reduced irrigation regimes were subjected to both low temperature and low moisture stress. The results of Table 3 clearly show that the addition of glycine betaine countered to some extent the effects of too low a temperature.

Conclusions that can be drawn from the results provided in Table 3 clearly indicate that the cotton crop was stressed due to imposed low moisture levels and cool conditions in that the minimum temperature fell below the threshold for growth of 12° C. on six of the 38 days over which the trial was conducted.

The response of cotton to glycine betaine varied with the dose supplied to the plants and with the stage of the crop at the time of application of the glycine betaine. As the dose was increased, the number of fruit forms retained on plants increased to a maximum and then decreased. Glycine betaine was found to have a true optimum dose when applied to cotton of around 3 kg per hectare when applied at 77 days after planting. At this time, the number of fruit forms increased by around 35% at 113 days after planting.

EXAMPLE 2

Boll retention, yield and quality were the criteria for selection of the optimum doses, time of application and adjuvants suitable for the commercial recommendation of glycine betaine.

A similar test plot to that of Example 1 was prepared and used in this example with a similar regime of treatment and application of betaine.

Application Timing

Glycine betaine retains cotton fruit in significant (P=0.05) responses to both the time of application and to dose. Time of application is the more important factor in increasing boll numbers. The applications at pre-squaring and first square did not significantly (P=0.05) improve boll numbers over the untreated. The optimum time of application was the onset of flowering, where 2% of plants were flowering and boll numbers increased by up to 22.7% over the untreated. Marginally fewer bolls were retained by common treatments applied at the latest application timing of early flowering, in comparison to the optimum timing. These later data were more variable and significance was attained only at the P=0.15 level (Table 4).

The optimum dose of glycine betaine required to increase boll numbers significantly (P=0.05) above that of untreated cotton, at the optimum early flowering application (T3), appeared to be within the 2.5 kg/ha to 3.5 kg/ha range. Lower doses did not significantly (P=0.05) improve boll numbers (Table 4).

TABLE 4

The Effect of Spray Timing of Glycine-betaine Upon Boll Retention in Irrigated Cotton cv.CS-50. Dalby.

| Dose of Glycine-betaine; Kg/Ha. | BOLLS PER METRE AT 145 DAYS AFTER EMERGENCE FROM FOUR TIMES OF APPLICATION | | | |
|---|---|---|---|---|
| | T1/presquaring | T2/first square | T3/preflowering | T4/early flowering |
| 0.0 | 135.6 a | 135.6 a | 135.6 a | 135.6 a |
| 0.5 | 135.0 a | 138.0 a | 145.1 ab | na |
| 1.5 | 137.9 a | 143.0 a | 150.0 ab | 147.7 a |
| 2.5 | 138.2 a | 143.2 a | 155.9 bc | 152.2 a |
| 3.5 | na | na | 166.5 c | 153.0 a |
| 7.0 | na | na | na | 160.4 a |
| P,F (treat). | 0.9 | 0.9 | 0.006 | 0.15 |
| LSD (P = 0.05) | — | — | 15.2 | — |

It is thought that at 145 DAE (days after emergence of the plants) glycine betaine appears to have improved early boll retention by affecting the complex of metabolic and environmental stresses that cause the shedding of squares and young bolls. Bolls older than 10 days usually do not shed. The pre-flowering application was made when one flower per 4 m was present, or at the initiating of flowering, approximately 7 days before 50% of the crop would support one flower.

Boll Maturity and Plant Height

The effect of glycine betaine when applied at the optimum time of very early flowering upon boll maturity was determined by the number and percentage of bolls open at 145 DAE. Glycine betaine did not significantly (P=0.05) improve maturity, although an extra 4 to 8 bolls per m were opened by the optimum dose range (Table 5). The dose of glycine betaine was highly significantly (P<0.01) and positively correlated with plant height at 145 DAE, where the optimum dose range promoted a significant (P=0.05) increase in height of 85 to 100 mm above that of untreated cotton (Table 5). The untreated cotton was not considered a tall crop at ca. 1.0 m in height.

The increases in boll retention found at 145 DAE due to the use of glycine betaine at the optimum application timing (Table 4) were not influenced by plant stand. No correlation was found between the variable, but not significantly different (P=0.05) plant populations of Table 5 and these boll numbers. Boll numbers per plant were significantly (P=0.05) and positively correlated with the dose of glycine betaine, however no difference between doses was detected (Table 5). A lack of correlation (r=0.009) was also found between plant population and height, ensuring that the increases in height found were not influenced by inter-plant competition and therefore attributable to glycine betaine.

TABLE 5

The Effect of Glycine-betaine Applied at the Initiation of Flowering (T3) Upon Boll Maturity in Irrigated Cotton cv.CS-50.

| Dose of Glycine betaine; Kg/Ha. | BOLLS AT 145 DAE | | | | | | |
|---|---|---|---|---|---|---|---|
| | No open/m | % open | Number Unharvestable/m | % Unharvestable | Number/plant | Plant Height m | Plants/m |
| 0.5 | 19.7a | 13.6a | 6.5a | 4.5a | 15.0a | 1.087a | 10.0a |
| 1.5 | 20.5a | 13.9a | 7.0a | 4.6a | 16.9a | 1.1ab | 9.0a |
| 2.5 | 19.0a | 12.1a | 6.4a | 4.1a | 21.0a | 1.1ab | 8.4a |
| 3.5 | 23.4a | 14.4a | 6.4a | 4.0a | 18.6a | 1.115ab | 9.2a |
| 0.0 | 15.2a | 11.2a | 6.1a | 4.6a | 16.1a | 1.015c | 8.6a |
| P,F (treat.) | 0.38 | 0.75 | 0.9a | 0.86 | 0.18a | 0.000 | 0.53 |
| LSD (P = 0.05) | — | — | — | — | — | 0.02 | — |

The data associated with boll maturity in Table 2, for the optimum application timing, was also collected for the other application timings and subjected to similar analyses. Some significant differences which were found are of interest.

Increases in maturity, in combination with increased retention (Table 4) only occurred after flowering has been initiated. Boll numbers indicated that the 2.5 to 3.5 kg.ha dose range was optimum when applied at the initiation of flowering. This is supported by the result that maturity is only marginally improved by application at the later time of early flowering. These maturity results, in combination with the increases in boll retention, suggest that an application of glycine betaine may be effective if made within a period around very early flowering.

Adjuvants and Conditions of Application

The effect of adjuvants and application conditions upon glycine betaine were evaluated in a trial laid down beside that which evaluated application timing and yield. Application was two days later than that trial, at approximately 5 days prior to 50% of the plants supporting a flower.

The treated boll number, irrespective of adjuvant, volume of application or condition of application, was 18% higher (P=0.009) than the untreated boll number, with means of 136.6 compared to 115.5 (Table 6). The use of wetter, mineral oil or vegetable oil, or the mixture of these adjuvants with glycine betaine, all provided higher boll retention than untreated cotton. However, no significant differences were found between any two of the 13 treatments in this trial. The increases in yield over untreated cotton vary from 11 to 23% (Table 6). The boll increase of ca. 23% in this trial for treatment 1 is commensurate with a 28% increase in boll number found in the neighbouring trial for the same 2.5 kg/ha plus wetter, 200 L/ha treatment.

TABLE 6

The Effect of Volume of Application, Drying Time of Spray Deposit, Wetting Agent and Oil Type upon Glycine-betaine in the Retention of Bolls in Irrigated Cotton, cv CS-50.

| Treatment applied with 2.5 Kg/Ha Glycine-b | Spray Volume L/Ha | Drying time of Deposit | Wetter, Plus 50 2 ml/L | DC-TRON min. oil 2 L/Ha | S/TROL veg. oil 2 L/Ha | 146 DAE Bolls/m | % Increase over Untreated |
|---|---|---|---|---|---|---|---|
| 1 | 200 | Slow | Yes | — | — | 142.0 | 22.9 |
| 2 | 50 | Fast | Yes | — | — | 137.0 | 18.6 |
| 3 | 100 | Fast | Yes | — | — | 138.0 | 19.4 |
| 4 | 200 | Fast | Yes | — | — | 127.8 | 10.8 |
| 5 | 50 | Fast | — | Yes | — | 139.0 | 20.3 |
| 6 | 100 | Fast | — | Yes | — | 131.4 | 13.7 |
| 7 | 200 | Fast | — | Yes | — | 130.7 | 13.2 |
| 8 | 50 | Fast | — | — | Yes | 134.5 | 16.4 |
| 9 | 100 | Fast | — | — | Yes | 138.8 | 18.2 |
| 10 | 200 | Fast | — | — | Yes | 134.0 | 16.0 |
| 11 | 50 | Fast | Yes | Yes | — | 142.4 | 23.2 |
| 12 | 50 | Fast | Yes | — | Yes | 140.1 | 21.2 |
| 13 | 0 | 0 | 0 | — | — | 115.5 | 0 |
| P,F (treat) | 0.45 | — | — | — | — | 0.328 | |
| LSD P = 0.05 | — | — | — | — | — | — | |

No significant differences (P=0.98) were detected between different treatment means. The trend is that the effect of wetting agent and mineral oil appears to decrease as the volume of application increases. Vegetable oil appears more suited to the higher volumes under fast drying conditions. The mean effect, irrespective of adjuvant, shows the acceptability of the 50 L/ha volume of application, as performance decreases marginally with an increase in volume of application. No significant differences (P=0.53) were detected between any two volumes of application.

At the 50 L/ha volume of application level, the performance of mineral oil and vegetable oil was improved by 2.9% and 4.8%, respectively, by the addition of wetting agent under fast drying conditions. Conversely, the performance of wetting agent was improved by 4.6% when mixed with mineral oil and 2.6% with vegetable oil.

lated with the dose of glycine betaine (Table 7). A dose range of 2.5 to 3.5 kg/ha was indicated at 145 DAE as an optimum for retaining bolls. This was reinforced at 187 DAE by the relative loss of bolls over the period 145 to 187 DAE, despite an odd response to dose. The optimum dose range lost 4 to 6.7% of bolls over 42 days in comparison to 16% for untreated cotton (Table 7).

The increase in boll numbers resulted in significant (P=0.05) increases in seed and lint in a highly significant (r=0.43, P<0.01) correlation to dose. At the indicated optimum dose range increases in yield of seed cotton (seed plus lint) of 22.9 to 37.6% were provided (Table 7).

TABLE 7

The Effect of Glycine-betaine Upon Boll Retention and Yield in Irrigated Cotton, cv CS-50.

| | DAYS AFTER EMERGENCE (DAE) | | | | | | | |
|---|---|---|---|---|---|---|---|---|
| Dose of Glycine - b Kg/Ha | YIELD COMPONENTS; 187 DAE | | | | | BOLLS PER METRE | | % Boll loss |
| | Seed | Lint | Seed + Lint | % increase over UTC | Pre-defoliation 145 DAE | Harvest 187 DAE | 145-187 DAE | |
| 0.0 | 240.7 a | 166.2 a | 406.9 a | 0.0 | 135.6 a | 112.5 a | 16.3 | |
| 0.5 | 270.0 a | 189.6 ab | 459.6 a | 12.2 | 145.1 ab | 135.4 b | 6.0 | |
| 1.5 | 264.7 a | 184.9 ab | 449.7 a | 10.5 | 150.0 ab | 129.2 ab | 12.6 | |
| 2.5 | 292.9 ab | 207.4 bc | 500.2 ab | 22.9 | 155.9 bc | 144.6 bc | 6.7 | |
| 3.5 | 324.6 b | 235.5 c | 560.1 b | 37.8 | 186.5 c | 158.6 c | 4.0 | |
| P.F (treat) | 0.044 | 0.021 | 0.032 | — | 0.008 | 0.006 | — | |
| LSD P = 0.05 | 54.15 | 40.27 | 94.17 | — | 15.2 | 22.68 | — | |

Yield

The boll numbers found at harvest were significantly correlated (r=0.34, P<0.05) with the boll numbers found at 145 DAE and highly significantly (r=0.54, P<0.01) corre- The effect of 7.0 kg/ha of glycine-betaine applied at early flowering was compared with the lower dose range applied at the earlier optimum time of pre-flowering. The earlier application of 3.5 kg/ha provided a significantly (P=0.05)

higher yield of seed cotton than the later application of 7.0 kg/ha (Table 8).

TABLE 8

The Effect of Glycine-betaine Upon Yield in Irrigated Cotton, cv CS-50

| Dose of glycine-betaine; Kg/Ha. | YIELD; gm/m. | | | % INCREASE OVER UNTREATED | | |
|---|---|---|---|---|---|---|
| | Seed | Lint | Seed + Lint | Seed | Lint | Seed + Lint |
| 0.0 | 240.7 a | 166.2 a | 406.9 a | 0.0 | 0.0 | 0.0 |
| 0.5 | 270.0 a | 189.6 ab | 459.6 ab | 12.2 | 14.1 | 13.0 |
| 1.5 | 264.7 a | 184.9 ab | 449.7 ab | 10.0 | 11.2 | 10.5 |
| 2.5 | 292.9 a | 207.4 ab | 500.2 bc | 21.7 | 24.8 | 22.9 |
| 3.5 | 324.6 a | 235.5 c | 580.1 c | 34.8 | 41.7 | 37.8 |
| 7.0 | 264.9 a | 188.9 ab | 453.8 ab | 10.0 | 13.8 | 11.5 |
| P,F (treat) | 0.06 | 0.025 | 0.04 | | | |
| LSD P = 0.05 | | 38.88 | 92.36 | | | |

Defoliation

Glycine betaine did not adversely affect defoliation in either the adjuvant or time of application trial. An assessment of leaves remaining in the latter trial on the day of test, 10 days after the first defoliation application of DROPP at 100 gm/ha plus 2 L/ha of DC-TRON showed that glycine betaine in face retained less leaves than the untreated (Table 9). The number of leaves remaining was highly significantly (r=0.5, P<0.01) and negatively correlated with the log (dose +1) of glycine betaine.

Crops which have a good load of early bolls often defoliate better than those which carry more, later set bolls. The response to the initial defoliation is considered to be due to the increased retention of bolls demonstrated at harvest (Table 7).

The second defoliation of DROPP at 120 gm plus DC-TRON at 2 L/ha was applied on this day and five days later all plots, including the untreated, were successfully and completely defoliated. Conditions at this time were warm and ideal for DROPP.

TABLE 9

The Effect of Glycine-betaine Upon Defoliation in Irrigated Cotton, cv CS-50.

| Dose of glycine-betaine; Kg/Ha. | 10 DAD(1)* Leaves per metre | 5 DAD(2)* Leaves per metre |
|---|---|---|
| 0.0 | 38.5a | <1 |
| 0.5 | 12.2b | <1 |
| 1.5 | 10.2b | <1 |
| 2.5 | 8.9b | <1 |
| 3.5 | 10.2b | <1 |
| 7.0 | 18.0b | <1 |
| P,F (treat) | 0.000 | 1.0 |
| LSD P = 0.05 | 9.3 | — |

*10 DAD = 10 days after the first defoliation
*Day of assessment
*5 DAD = 5 days after the second defoliation Results
Application Timing/Dose The results were clear. Glycine betaine retains bolls in significant (P=0.05) responses to both the time of application and to dose. Considering the effects upon boll retention, boll maturity and yield, the optimum time to apply glycine betaine was over the period from the initiation of lowering, where 1 flower per 3.4 m was present to a time 5 to 7 days later. The optimum dose was within the range 2.5 to 3.5 kg/ha inclusive. This range increased boll numbers by 21.7% to 34.8%, resulting in an increase of yield of 22.9% to 37.6% in seed cotton, respectively.

Boll Maturity and Plant Height

The optimum use of glycine betaine did not significantly (P=0.05) improve the maturity of early bolls or promote unharvestable bolls. The optimum dose range promoted a significant (P=0.05) increase in the height of cotton of 85 to 100 mm.

Adjuvants

Wetting agent appeared as the most cost effective adjuvant for recommendation for use with glycine betaine. Applications with wetting agent preferably should be made under slow drying conditions. The 50 L/ha volume of application appears entirely acceptable and more practical than 100 L/ha for recommendation for ground application in cotton. Under fast drying conditions either vegetable oil or mineral oil, plus wetting agent should be used. Sprays should be directed at the plant parts which take up the material, presumedly leaves. The lack of significant differences detected in this trial are due largely to excessive variation in boll numbers, indicating that a much larger sample of boll numbers was required.

Volumes of 20 L/ha or less should be investigated for aerial application, preferably as an aqueous, oil protected ULV.

Yield

Clear results were obtained. Glycine betaine significantly (P=0.05) increased the retention of bolls resulting in significant (P=0.05) increases in yield of 22.9 to 37.6% at the optimum dose range of 2.5 to 3.5 kg/ha, respectively. While boll number and seed and lint production per meter were significantly increased, boll weight was only marginally increased, in a non-significant (P=0.05) improvement.

The contribution of the bottom, middle and top bolls was not investigated in this trial in a season of low micron. It is now apparent that this needs to be established as low micron late, immature bolls may be held by glycine betaine and the ability to produce high micron lower bolls may have been masked in this season. Conversely, used in an environment of high micron, albeit location, variety or season, glycine betaine may reduce micron. The penalty discounts for this are inconsequential under high prices and the increase in yield may adequately offset such penalties. When cotton prices drop such penalties assume more importance. However, the misuse of PIX, which promotes the retention of late season bolls, is of concern to growers and ginners.

Some scope may exist for using glycine betaine under very high plant populations to promote only early, high quality bolls where extra inter-plant competition may limit the production of late bolls.

Defoliation

Glycine betaine does not adversely affect defoliation with DROPP. Increased boll retention significantly (P=0.05) aided the first defoliation, probably by forcing greater demand upon the plant system. Undoubtedly water and nutrition management has an influence upon this aspect. Treated and untreated plots were equally well defoliated after the second defoliation when conditions were good for the use of DROPP. The increase in plant height found with glycine betaine did not affect defoliation.

Advantages of the present invention include being able to control the adverse effects of stress induced in growing cotton plants by such factors as too little water and moisture, too much water and moisture, too high salt, too low a temperature, and the like. Cotton plants treated in accordance with the present invention are thought to be more disease resistant and are more resistant to infection from diseases or pests as a reduced number of plants damaged by disease or pests were identified in the trials.

Other advantages of using glycine betaine as an osmolyte regulator in accordance with the present invention include (i) an increase in yield of the cotton plants, (ii) that there is no adverse effect on quality, (iii) that the results of experimental work confirm that the yield actually obtained can be predicted from an increase in the number of bolls present as the development of bolls after initiation is not adversely affected by the use of glycine betaine, (iv) that there is an increase in plant height, (v) that desired defoliation was enhanced as a result of the first defoliation application to improve the quality of the yield.

The described arrangement has been advanced by explanation and many modifications may be made without departing from the spirit and scope of the invention which includes every novel feature and novel combination of features hereindisclosed.

Those skilled in the art will appreciate that the invention described herein is susceptible to variations and modifications other than those specifically described. It is understood that the invention includes all such variations and modifications which fall within the spirit and scope.

I claim:

1. A method of improving growth of cotton plants by controlling stress in the growing cotton plants comprising administering an effective amount of a betaine to the plant wherein stress induced or developing in the plant can be controlled in order to enhance the growth of the plant to provide a greater yield, or to enable the plant to mature more quickly, or both, thereby increasing the economic value of the plant.

2. The method according to claim 1 in which the betaine is administered alone.

3. The method according to claim 1 in which the betaine is administered with an other material selected from a wetting agent, an adjuvant, a defoliant, a growth regulator, a pesticide, or a nutrient.

4. The method according to claim 3 in which the other material can be added separately or in combination with the betaine.

5. The method according to claim 3 in which the betaine and other material have a synergistically beneficial effect on the plant.

6. The method according to claim 4 in which the betaine and the wetting agent are applied to the plant together, or the betaine, the wetting agent, a mineral oil and/or a vegetable oil are applied to the plant in combination.

7. The method according to claim 6 in which the mineral oil is a clear mineral oil which is miscible with water and the vegetable oil is rapeseed vegetable oil.

8. The method according to claim 1 in which the stress is selected from the group consisting of environmental stress, temperature stress, water stress, salinity stress, light stress and nutritional stress.

9. The method according to claim 1 in which the betaine is administered to the plant in a dosage of from about 0.1 to 30.0 kg/ha.

10. The method according to claim 9 in which the betaine is administered to the plant in a dosage of from 0.1 to 20.0 kg/ha.

11. The method according to claim 9 in which the betaine is administered to the plant in a dosage of from 0.5 to 7.0 kg/ha.

12. The method according to claim 9 in which the betaine is administered to the plant in a dosage of from 2.0 to 4.0 kg/ha.

13. The method according to claim 9 in which the betaine is administered to the plant in a dosage of from 2.5 to 3.5 kg/ha.

14. The method according to claim 9 in which the betaine is applied externally or exogenously to the plant.

15. The method according to claim 14 in which the betaine is applied to the leaves of the plant by spraying.

16. The method according to claim 1 in which the cotton plant belongs to the species Siokra L-22, Siokra L-23, or CS-50.

17. The method according to claim 1 in which the betaine is administered to the plants at any time from planting until harvesting.

18. The method according to claim 17 in which the betaine is applied to the cotton plants at from 77 to 98 days after planting.

19. The method according to claim 17 in which the betaine is applied to the plants in the period from the initiating of flowering of the plants until a time from about 5 to 7 days later when there is significant flowering.

20. The method according to claim 15 in which the betaine is applied to the plants by spraying in the form of an aqueous solution.

21. The method according to claim 20 in which the aqueous solution has a concentration of betaine of about 3.0 kg per 100 L of water.

22. The method according to claim 21 in which the aqueous solution of betaine is applied to the plants in an amount of from about 50 to 200 L/ha.

23. The method according to claim 21 in which the aqueous solution of betaine is applied to the plants in an amount of from about 50 L/ha to 100 L/ha.

24. The method according to claim 14 in which the betaine is applied to the growing plants in a single application or in two or more separate applications over a period of time.

25. The method according to claim 1 in which the betaine is glycine betaine.

26. The method according to claim 25 in which the glycine betaine is applied to cotton in a dosage of from 2.0 kg/ha to 4.0 kg/ha in the period from the initiation of flowing until up to 7 days after the initiation of flowering.

27. The method according to claim 24 in which the betaine is applied in several batches, the first batch being applied prior to flowering, and another batch being applied to the plants at the initiation of flowering.

* * * * *